United States Patent [19]

Sharif et al.

[11] Patent Number: 4,584,419

[45] Date of Patent: Apr. 22, 1986

[54] PROCESS FOR THE PRODUCTION OF BUTANE-1,4-DIOL

[75] Inventors: Mohammad Sharif, Middlesbrough; Keith Turner, Stockton-on-Tees, both of England

[73] Assignee: Davy McKee Ltd., London, England

[21] Appl. No.: 673,797

[22] Filed: Nov. 21, 1984

[30] Foreign Application Priority Data

Nov. 29, 1983 [GB] United Kingdom ............... 833/1793

[51] Int. Cl.$^4$ ..................... C07C 29/136; C07C 31/20
[52] U.S. Cl. .................................... 568/864; 549/326
[58] Field of Search ................................ 568/864, 885

[56] References Cited

U.S. PATENT DOCUMENTS 4,112,245 9/1978 Zehner et al. ...................... 568/864

FOREIGN PATENT DOCUMENTS 0060787 9/1982 European Pat. Off. ............ 568/864
26605 11/1968 Japan ................................... 568/864
555240 8/1943 United Kingdom ................ 568/864

Primary Examiner—J. E. Evans
Attorney, Agent, or Firm—Bernard, Rothwell & Brown

[57] ABSTRACT

A process for the production of butane-1,4-diol comprises hydrogenating a di($C_1$ to $C_3$ alkyl) ester of a $C_4$ dicarboxylic acid, e.g. an ester of a but-2-en-1,4-dioic acid, such as diethyl maleate, in the vapor phase at a temperature of from about 150° C. to about 240° C. and at a pressure in the range of from about 25 bar to about 75 bar in the presence of a reduced copper chromite catalyst, and recovering resulting butane-1,4-diol containing reaction product. The catalyst contains, before reduction, from about 25 to about 45% by weight of copper and from about 20 to about 35% by weight of chromium and preferably has an internal surface area of at least about 30 sq. m. per gram. The process is preferably conducted in two or more reaction zones, which are preferably operated adiabatically, the feed temperature to the first zone being higher than that to at least one subsequent reaction zone.

11 Claims, 1 Drawing Figure

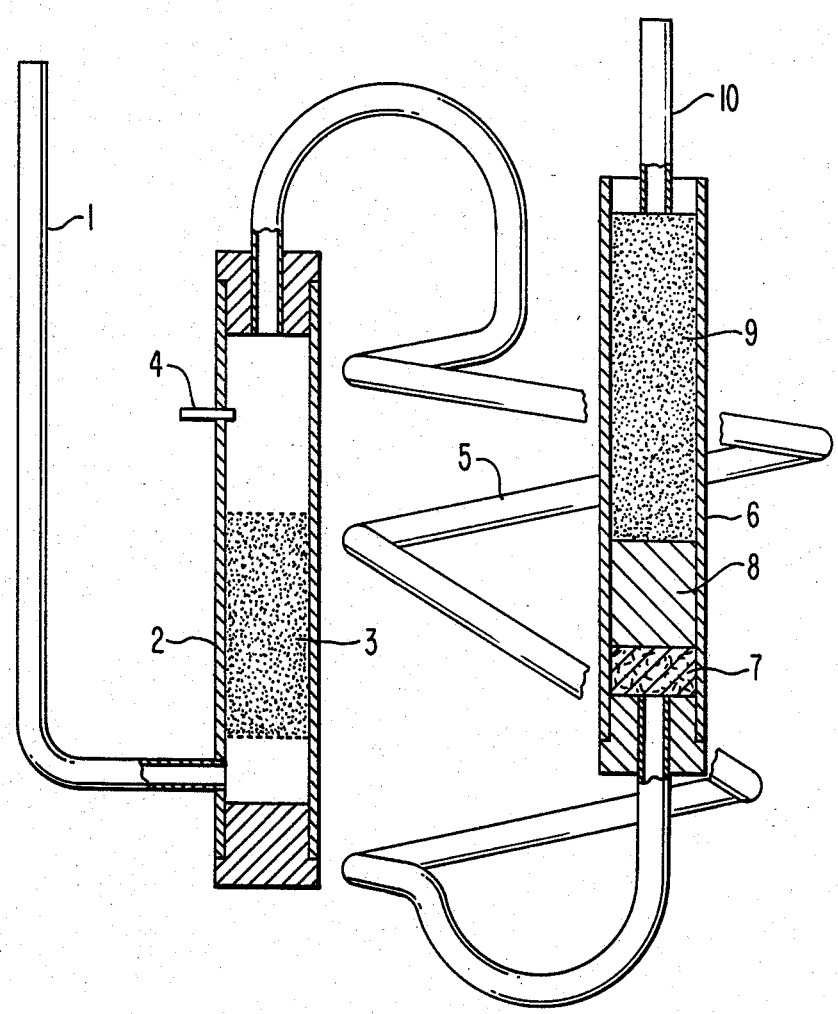

PROCESS FOR THE PRODUCTION OF BUTANE-1,4-DIOL

This invention relates to a process for the production of butane-1,4-diol, more particularly to a process for the production of butane-1,4-diol by hydrogenolysis of a di-($C_1$ to $C_3$ alkyl) ester of a $C_4$ dicarboxylic acid, such as maleic acid, fumaric acid, or succinic acid.

Butane-1,4-diol is used as a monomer in the production of plastics such as polybutylene terephthalate. It is also used as an intermediate for manufacture of butyrolactone and of the important solvent, tetrahydrofuran.

The most commonly adopted present method of manufacturing butane-1,4-diol involves reacting acetylene and formaldehyde by the Reppe reaction to give but-2-yne-1,4-diol which is then hydrogenated to form butane-1,4-diol.

Alternatively it has been proposed in European Patent No. 0018163 to react allyl alcohol, which can be produced from propylene, with iso-butylene to form allyl t-butyl ether. This compound is then hydroformylated using, for example a rhodium complex hydroformylation catalyst to give 4-t-butoxybutyraldehyde, which is then hydrogenated and cleaved under mild conditions with the aid of an acid catalyst to give butane-1,4-diol and iso-butylene which is recycled for reaction with further allyl alcohol.

There have also been a number of proposals to produce butane-1,4-diol from maleic anhydride. According to these proposals maleic anhydride, which is produced by oxidation of butane or benzene, is esterified to give a diester of maleic acid which is then hydrogenated in one or more stages to give butane-1,4-diol. Alternatively it is proposed that, maleic acid or anhydride should be directly hydrogenated. In some of these proposals butyrolactone is an intermediate product.

U.S. Pat. No. 4,001,282 describes a process for production of butyrolactone by passing vaporised maleic acid, maleic anhydride, or a mixture thereof together with water and hydrogen over a metallic catalyst capable of hydrogenolysing a carboxylic group to a hydroxymethyl group. Typical catalysts include copper-zinc catalysts (such as Girdler G-66 ARS and G-66-BRS) and copper chromite catalysts (such as Girdler G-13). Besides butyrolactone the reported products include succinic acid anhydride, propionic acid, butyric acid, propanol and n-butanol, but no mention is made of butane-1,4-diol.

U.S. Pat. No. 4,048,196 teaches production of butane-1,4-diol and/or tetrahydrofuran by multi-stage catalytic hydrogenation of maleic anhydride or succinic anhydride. In a first liquid phase hydrogenation step maleic anhydride or succinic anhydride is hydrogenated over a nickel catalyst to give butyrolactone. This is then hydrogenated in the liquid phase over a copper/zinc oxide or hydroxide catalyst to give butane-1,4-diol and tetrahydrofuran.

In U.S. Pat. Nos. 4,083,809 and 4,105,674 and in British Patent Specification No. 1534136 there is described a process for producing butyrolactone using a Cu-Pd catalyst for vapour phase hydrogenation of maleic acid, succinic acid, their anhydrides, and mixtures of two or more thereof.

U.S. Pat. No. 2,079,414 describes use of copper chromite as a catalyst for effecting hydrogenation of esters. It is recommended that, in operating in the vapour phase, temperatures within the range of 300° C. to 400° C. should be used.

U.S. Pat. No. 2,040,944 recommends use of temperatures of 230° C. to 400° C. for hydrogenation of esters of non-aromatic polybasic acids with a monohydric aliphatic alcohol containing at least four carbon atoms. It recommends copper chromite as catalyst and teaches that the catalyst can be prepared by ignition of a copper ammonium chromate precipitate and used without further treatment or after reduction by hydrogen at a temperature of 500° C. or higher. It goes on to mention that either the liquid phase or vapour phase can be used, depending largely upon the ester to be hydrogenated. Pressures of 100 to 250 bar are recommended, as well as use of about 5 to 20 moles of hydrogen per mole of ester. An example is given of a liquid phase batch reaction in which crude butyl succinate is hydrogenated at 3000 p.s.i.g. (207 bar) at 255° C. using a copper chromite catalyst.

A discussion of the use of copper chromite as a catalyst for hydrogenation of esters is to be found in "Organic Reactions", Vol. 8, published in 1954 by J. Wiley and Sons, Inc.. Chapter 1 of this reference book is by Homer Adkins and is entitled "Catalytic Hydrogenation of Esters to Alcohols". Table II on page 15 lists two experiments in which diethyl succinate is reacted at 5000 p.s.i. (345 bar) and 150° C. for 4 hours and at 3300 p.s.i. (227.5 bar) and 250° C. for 6.5 hours respectively. This reference suggests that the "copper chromite" catalyst is more correctly described as an approximately equimolecular combination of cupric oxide and cupric chromite, i.e. $CuO, CuCr_2O_4$.

Production of butane-1,4-diol and tetrahydrofuran by a process in which a dialkyl maleate is subjected to hydrogenolysis in the liquid phase in the presence of a copper chromite catalyst is described in British Patent Specifications Nos. 1454440 and 1464263. A similar liquid phase process using nickel-based catalysts is described in British Patent No. 1587198.

Butyrolactone is produced, according to British Patent Specification No. 1168220, by vapour phase hydrogenation of maleic anhydride, succinic acid, an ester of maleic acid, an ester of succinic acid, or an ester of fumaric acid in the presence of a copper-zinc catalyst to which may be added small amounts of one or more promoters other than chromium. This specification mentions that the preparation of butyrolactone by hydrogenation of the chosen starting materials was already known and states (see page 1, lines 23 to 25):

"It is also possible to carry out the hydrogenation in the vapour phase when the preferred catalyst is copper-chromite."

The patentees continue (see page 1, lines 29 to 39):

"Furthermore hitherto known hydrogenation processes in the vapour phase suffer from the disadvantage of having to be carried out at a relatively high temperature, for example, about 300° C., and moreover in order to obtain a good conversion rate, the reaction material should be fed to the catalyst at low speed. It is also difficult to reactivate the copper-chromite catalyst, when the activity has been lowered by use for a period of time."

It is an object of the present invention to provide a novel improved process for the production of butane-1,4-diol using as a starting material a precursor that can be produced from maleic anhydride and hence ultimately from butane or benzene as feedstock.

According to the present invention there is provided a process for the production of butane-1,4-diol which comprises hydrogenating a di-($C_1$ to $C_3$ alkyl) ester of a $C_4$ dicarboxylic acid in the vapour phase at a temperature of from about 150° C. to about 240° C. and at a pressure in the range of from about 25 bar to about 75 bar in the presence of a reduced copper chromite catalyst which contains, before reduction, from about 25 to about 45% by weight of copper and from about 20 to about 35% by weight of chromium, and recovering resulting butane-1,4-diol containing reaction product.

Preferably the ester is a di-($C_1$ to $C_3$ alkyl) ester of a but-2-en-1,4-dioic acid or of succinic acid.

The invention is based upon the surprising discovery that hydrogenation can be carried out right through to butane-1,4-diol in high yield by effecting catalytic hydrogenation of a di-($C_1$ to $C_3$ alkyl) maleate, fumarate, succinate or mixture thereof in the vapour phase under carefully selected conditions using a reduced copper chromite hydrogenation catalyst of carefully controlled composition.

In a commercial plant the process will normally be operated on a continuous basis. Often it will be preferred to employ at least two hydrogenolysis zones, each containing a charge of copper chromite catalyst, connected in series.

In operating the process of the invention it is preferred to operate at a temperature no higher than about 220° C., for example in the range of from about 150° C. to about 210° C. The most preferred temperature range is from about 170° C. to about 190° C. The preferred operating pressure is preferably not more than about 50 bar, and is most preferably in the range of from about 35 bar to about 45 bar. Usually it is at least 30 bar.

The or each hydrogenolysis zone may comprise a tubular or multi-tubular reactor which is operated under substantially isothermal conditions. However it is preferred to operate under adiabatic conditions in the or each hydrogenolysis zone.

The dialkyl ester of a $C_4$ dicarboxylic acid used in the process of the invention is derived from an alkyl alcohol containing from 1 to 3 carbon atoms. Examples of such esters include diethyl maleate, diethyl fumarate, diethyl succinate, and mixtures of two or more thereof. Other suitable esters include the dimethyl, di-n-propyl, and di-i-propyl esters of maleic, fumaric and succinic acids, as well as mixtures thereof.

Besides using the substantially pure ester as feedstock it is also possible to use a solution of the ester in a suitable inert solvent, e.g. methanol, ethanol, or n- or iso-propanol. Thus a preferred method of producing dialkyl maleates involves esterification of maleic anhydride with an excess of an appropriate alkanol, such as ethanol. This may result in formation of a mixture of dialkyl maleate and alkanol (e.g. a mixture of diethyl maleate and ethanol) containing, for example, from about 5% up to about 60% by weight by weight of alkanol. Such mixtures can be used in the process of the present invention without further purification.

The ester or ester solution feed can be admixed with recycled unconverted starting ester recovered in the product recovery section of the plant. If a di-($C_1$ to $C_3$ alkyl) maleate or fumarate is used as starting material, then the product stream may include the corresponding diethyl succinate; this can be recycled from the product recovery section of the plant for admixture with the ester or ester solution feed. In some cases it may also be desirable to recycle at least a part of the butane-1,4-diol product and/or of the byproduct gamma-butyrolactone from the product recovery section for admixture with the ester or ester solution feed.

The process requires that the ester and any other condensible component present be in the vapour phase. This means that the composition of the vaporous mixture must be controlled so that, under the selected operating conditions, the temperature of the mixture in contact with the catalyst is always above the dew point of the ester and of any other condensible component present. This can normally be achieved by selecting an appropriate gas:ester ratio in the vaporous mixture. A convenient method of forming a vaporous mixture for use in the process of the invention is to spray the liquid ester or ester solution into a stream of hot hydrogen-containing gas so as to form a saturated or partially saturated vaporous mixture. Alternatively such a vaporous mixture can be obtained by bubbling a hot hydrogen-containing gas through a body of the liquid ester or ester solution. If a saturated vapour mixture is formed it should then be heated further or diluted with more gas so as to produce a partially saturated vaporous mixture prior to contact with the catalyst.

Reduction of a maleate or fumarate ester to butane-1,4-diol involves reaction of 5 moles of $H_2$ with each mol of ester, according to the following equation:

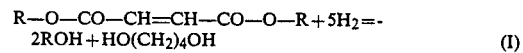

$$R-O-CO-CH=CH-CO-O-R + 5H_2 = 2ROH + HO(CH_2)_4OH \quad (I)$$

where R is an alkyl radical containing from 1 to 3 carbon atoms.

However, when a succinate ester is hydrogenolysed, only 4 moles of $H_2$ are consumed:

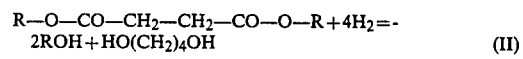

$$R-O-CO-CH_2-CH_2-CO-O-R + 4H_2 = 2ROH + HO(CH_2)_4OH \quad (II)$$

where R is as defined above.

The vaporous mixture will normally contain excess hydrogen. It may additionally contain a minor amount of carbon oxides. The vaporous mixture may further include vaporised inert solvent (if used) and one or more inert gases (e.g. $N_2$, A, $CH_4$ etc.) which may be present in the hydrogen supply in a major or minor amount. It may also include vaporous material recycled from the product recovery section. Preferably the hydrogen supply is substantially free from sulphur compounds, from halogens such as $Cl_2$, and from halogen containing compounds.

In the vaporous mixture the $H_2$:ester molar ratio is typically at least about 100:1 up to about 800:1 or more. Preferably it is at least about 150:1, and typically is at least 200:1. The most preferred range is from about 250:1 to about 450:1, although in many cases it is no higher than about 400:1.

In practice the reduction of a maleate ester, such as diethyl maleate, is more complex than is suggested by equation (I) above and results in production of variable amounts of by-products, including tetrahydrofuran, gamma-butyrolactone and n-butanol. Although the reaction mechanism has not been fully elucidated yet, the currently available evidence is consistent with the following sequence:

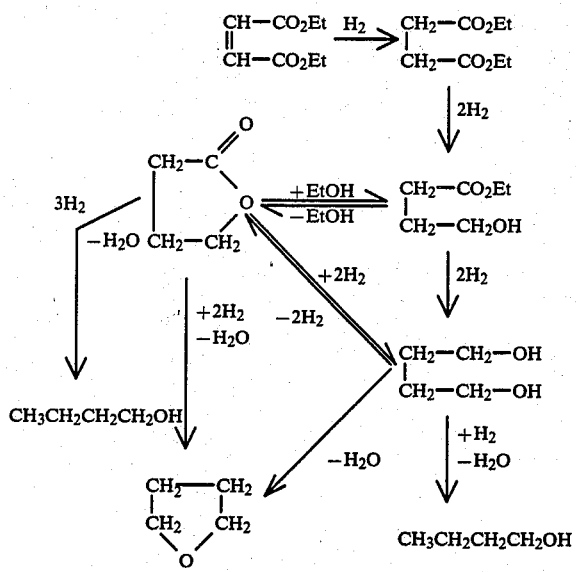

The catalyst is a reduced copper chromite catalyst. This should be prepared by careful reduction of copper chromite prior to use. Preferably the catalyst is reduced at a temperature of not more than about 200° C., for an extended period using a mixture of $H_2$ and an inert gas, such as nitrogen, methane or argon. A typical gas used for reduction of the catalyst is an $H_2$ in $N_2$ mixture containing, for example, from about 1% up to about 15% by volume of $H_2$. Usually the catalyst is reduced for at least about 24 hours prior to use. Best results are obtained when reduction is effected for several days at a temperature of from about 120° C. to about 180° C. prior to use in the process of the invention. It will usually be unnecessary to exceed about 10 days reduction pre-treatment. If the catalyst is reduced at a temperature in excess of about 200° C., the activity is noticeably inferior to the activity obtained by reduction at lower temperatures. If the catalyst is supplied in pre-reduced form then the period of reduction can be shorter. In the later stages of pre-treatment higher $H_2$ concentrations can be used; thus $H_2$ can replace the $H_2/N_2$ mixture towards the end of the reduction pre-treatment. It is best to use an elevated pressure during this pre-treatment period; for example, pressures of from 1 bar up to about 50 bar or higher can be used. After the reduction treatment the catalyst should be maintained under an inert gas, a hydrogen/inert gas mixture or hydrogen until use.

The formula of copper chromite may be written as $CuCr_2O_4$. However, it is known that copper chromite is non-stoichiometric and some authors have, for example, described a copper chromite catalyst as copper chromium oxide of the formula $CuO.CuCr_2O_4$. Thus the catalyst may contain an excess of copper oxide. It may further or alternatively contain a minor amount of at least one stabilizer, such as barium or manganese. The catalyst contains, before reduction, from about 25 to about 45% by weight of copper and from about 20 to about 35% by weight of chromium. The most preferred catalysts are those containing from about 32 to about 38% by weight of copper and from about 22 to about 30% by weight of chromium. Such catalysts preferably contain no more than about 15% by weight of a stabilizer or stabilizers, if present. It may be supported on a suitable inert carrier. Desirably the catalyst is in finely divided form having an internal surface area, as measured by the well-known BET method, of at least about 30 sq. m. per gram and preferably at least about 60 sq. m. per gram. Preferably it is formed into cylindrical pellets or into other conventional catalyst shapes, such as rings, saddles, or the like.

The ester is preferably supplied to the catalytic reaction zone (or, if there is more than one such zone, to each catalytic zone) at a rate corresponding to a liquid hourly space velocity in the range of from about 0.1 to about 0.6 $hr^{-1}$. In other words the liquid ester is supplied to the vaporization zone at a rate of from about 0.1 to about 0.6 unit volumes of ester per unit volume of catalyst per hour. This normally corresponds to a gaseous hourly space velocity in the range of from about 2500 to about 85,000 $hr^{-1}$, most preferably in the range of from about 8000 to about 30,000 $hr^{-1}$. By the term "gaseous hourly space velocity" we mean the number of unit volumes of vaporous mixture measured at 1 bar and 0° C. passed over a unit volume of catalyst per hour.

According to a preferred procedure the process of the invention is carried out using at least two hydrogenolysis zones in sequence, the feed temperature to the first zone being higher than the feed temperature to at least one subsequent hydrogenolysis zone. Conveniently there are two hydrogenolysis zones connected in series with a cooling zone between them. However more than two hydrogenolysis zones can be provided, if desired, with a cooling zone between each successive pair of zones. Preferably each hydrogenolysis zone is operated under adiabatic conditions. The feed temperature to the first hydrogenolysis zone is typically selected to maximise conversion of the ester in that zone to butane-1,4-diol and gamma-butyrolactone. Preferably the feed temperature to the first hydrogenolysis zone does not exceed about 190° C. and even more preferably is in the range of from about 170° C. to about 190° C. Although a feed temperature in excess of about 190° C. can be used, if desired, to the first hydrogenolysis zone, this tends to result in an increase in formation of by-product tetrahydrofuran. For this reason it is preferred to operate with a feed temperature of not higher than about 190° C. to the first hydrogenolysis zone. In the second hydrogenolysis zone the feed temperature is typically selected to convert as much gamma-butyrolactone as possible to butane-1,4-diol.

Usually the feed temperature to the second hydrogenolysis zone is not more than about 175° C. and even more preferably lies in the range of from about 160° C. to about 175° C. If, however, the plant operator wishes to produce more gamma-butyrolacetone at the expense of butane-1,4-diol, the feed temperature to the second hydrogenolysis zone can be raised somewhat. In this case the feed temperature to the second zone can exceed about 175° C. and can be as high as that to the first zone.

Thus according to a particularly preferred aspect of the present invention there is provided a continuous process for the production of butane-1,4-diol which comprises:

providing a plurality of hydrogenolysis zones, including a first hydrogenolysis zone and at least one other hydrogenolysis zone connected in series therewith, each of which contains a charge of a reduced copper chromite catalyst which contains, before reduction, from about 25 to about 45% by weight of copper and from about 20 to about 35% by weight of chromium;

supplying to the first hydrogenolysis zone at a temperature of from about 170° C. to about 190° C. a vaporous feed stream containing hydrogen and a di-($C_1$ to $C_3$ alkyl) ester of a $C_4$ dicarboxylic acid at an $H_2$:ester molar ratio of from about 150:1 to about 800:1 and at a rate corresponding to a liquid hourly space velocity of the ester of from about 0.1 to about 0.6 $hr^{-1}$;

supplying to the other, or to each other, hydrogenolysis zone at a temperature in the range of from about 160° C. to about 175° C. a vaporous stream comprising reaction products from the immediately preceding hydrogenolysis zone;

maintaining the plurality of hydrogenolysis zones at a pressure in the range of from about 25 bar to about 75 bar; and recovering a product mixture containing butane-1,4-diol.

Care must be taken to keep the feed temperature to the second and any subsequent hydrogenolysis zone above the dew point of the ester and any other condensible component at all times.

If desired further gas and/or ester can be admixed with the product stream from the preceding zone prior to admission to the next zone in order to adjust the temperature or the $H_2$:ester molar ratio. It is also contemplated that one or more materials recovered from the prouct recovery section of the plant (e.g. dialkyl succinate, unreacted dialkyl maleate or fumarate, gamma-butyrolactone and/or butane-1,4-diol) can be admixed with the product stream from one zone prior to admission to the next succeeding zone, instead of or in addition to recycling such material to the inlet end of the first hydrogenolysis zone.

The product mixture exiting the catalytic reaction zone, or, if there is more than one hydrogenolysis zone, the final zone, contains, in addition to unreacted hydrogen and possibly other gases, a mixture of condensible materials including butane-1,4-diol and $C_1$ to $C_3$ alkyl alcohol derived from the alkyl moiety of the di-($C_1$ to $C_3$ alkyl) ester starting material. The condensible materials may further include butyrolactone, dialkyl succinate and possibly also a small amount of unreacted ester and minor amounts of byproducts. These condensible materials are preferably condensed from the product mixture and separated in any suitable fashion, e.g. by distillation in one or more stages under normal, elevated or reduced pressure. In designing a suitable product recovery system, it should be borne in mind that some of the components present in the product mixture are capable of forming azeotropic mixtures with one or more other components of the product mixture. The liquid butane-1,4-diol product and any butyrolactone formed can be passed forward for purification whilst any minor byproducts can be used as fuel for the process. The alkyl alcohol can be recycled for reaction with further maleic or succinic anhydride or with further fumaric acid to form fresh di-($C_1$ to $C_3$ alkyl) $C_4$ dicarboxylic acid ester for use in the process of the invention. Any unreacted starting ester (e.g. dialkyl maleate) and/or intermediate ester (e.g. dialkyl succinate) can be recycled for admixture with the ester or ester solution feed. If desired some of the butane-1,4-diol, and/or gamma-butyrolactone byproduct, can be recycled for admixture with the product stream from the first hydrogenolysis zone, or from an intermediate hydrogenolysis zone, of a plant with a plurality of hydrogenolysis zones.

The invention is further described in the following Examples. The compositions of catalysts A to D used in the Examples are listed in Table I.

TABLE I

| Catalyst | Composition (wt %) | | | | Surface Area ($m^2/g$) |
|---|---|---|---|---|---|
| | Cr | Cu | Mn | Ba | |
| A | 25 | 35 | — | — | 85 |
| B | 27 | 42 | — | — | 40 |
| C | 27 | 33 | — | 11 | 60 |
| D | 31 | 35 | 2 | 2 | 57 |

EXAMPLE 1

The apparatus is illustrated diagrammatically in the drawing. This was constructed out of stainless steel and was immersed in a fluidised sand bath (not shown) for heating purposes.

Hydrogen was introduced by way of a pressure regulator and flow controller (not shown) through line 1 to the bottom end of a vaporiser 2 containing a number of steel balls 3. Ester was metered as a liquid to vaporiser 2 through line 4. The resulting vaporous mixture of ester and hydrogen was passed through preheating coil 5 to reactor 6. This contained a layer 7 of glass balls, on which rested the catalyst bed 8. The remainder of the reactor was filled with glass balls 9 and the upper end of the reactor was fitted with an exit tube 10 which led to a condenser (not shown) and then to a pressure let-down valve (not shown).

The exit gas flow rate was measured downstream from the condenser using a wet gas meter (also not shown).

A charge of 30 ml of a granulated copper chromite catalyst (designated as catalyst A in Table I) was placed in the reactor which was then purged with nitrogen at 42 bar. The sand bath was raised to a temperature of 175° C. A 2% $H_2$ in $N_2$ gaseous mixture at 42 bar was then passed over the catalyst for 8 hours, followed by 10% $H_2$ in $N_2$ (still at 42 bar) for a further 16 hours, and then by pure $H_2$ (also at 42 bar) for an additional 12 hours.

Diethyl maleate was then introduced into the vaporiser at a rate of 10.2 ml/hr corresponding to a liquid hourly space velocity of 0.34 $hr^{-1}$. The $H_2$:ester molar ratio in the vaporous mixture was 359:1. The temperature of the sand bath was maintained at 175° C. The condensate was analysed by gas chromatography using a 1.82 meter long stainless steel column with an internal diameter of 3.18 mm containing 10% diethylene glycol succinate on Chromosorb PAW, a helium gas flow rate of 30 ml/minute and a flame ionisation detector. The instrument was fitted with a chart recorder having a peak integrator and was calibrated using a mixture of diethyl maleate, dialkyl succinate, butyrolactone, butane-1,4-diol, tetrahydrofuran and water of known composition. The exit gas was also sampled and analysed by gas chromatography using the same technique. The identity of the peaks was confirmed by comparison of the retention times observed with those of authentic specimens of the materials in question and by mass spectroscopy. The following compounds were detected in the reaction mixture: diethyl succinate, butyrolactone, butane-1,4-diol, tetrahydrofuran and water. Trace amounts of minor byproducts, including 2-ethoxytetrahydrofuran and 2-ethoxybutane-1,4-diol were also detected in the reaction mixture. From the results obtained it appeared that diethyl maleate had been smoothly converted to diethyl succinate, 95.5 mol % of which had then been converted to products with a selectivity to tetrahydrofuran of 4.3 mol %, a selectivity to n-butanol of 0.2 mol %, a selectivity to gamma-butyrolactone of 16.0 mol %, and a selectivity to butane-1,4-diol of 79.3 mol %, the balance being minor byproducts.

EXAMPLES 2 to 6

Using a similar procedure to that described in Example 1 five further runs were carried out, all at 42 bar, using 15 ml of copper chromite catalyst (catalyst A whose composition is listed in Table I). The results are listed in Table II.

TABLE II

| Example No. | Temp. °C. | $H_2$:ester molar ratio | LHSV $hr^{-1}$ | Ester Conversion (mol %) | Selectivity (mol %) | | | |
|---|---|---|---|---|---|---|---|---|
| | | | | | THF | BuOH | BL | BD |
| 2 | 179 | 279:1 | 0.32 | 95.3 | 4.7 | 0.2 | 17.4 | 77.4 |
| 3 | 181 | 237:1 | 0.53 | 86.6 | 4.2 | 0.2 | 21.4 | 74.0 |
| 4 | 175 | 312:1 | 0.16 | 98.7 | 4.4 | 0.2 | 16.7 | 78.5 |
| 5 | 175 | 299:1 | 0.34 | 91.4 | 2.8 | 0.1 | 16.8 | 80.1 |
| 6 | 175 | 255:1 | 0.33 | 86.6 | 4.0 | 0.1 | 20.3 | 75.4 |

Notes:
LHSV = liquid hourly space velocity
THF = tetrahydrofuran
BuOH = n-butanol
BL = gamma-butyrolactone
BD = butane-1,4-diol.

EXAMPLES 7 and 8

The charge of copper chromite catalyst used in Examples 1 to 6 was replaced by 15 ml of a barium-promoted copper chromite catalyst (catalyst C of Table I). The results are listed in Table III. The selectivities to minor byproducts are not listed.

TABLE III

| Example No. | Temp. °C. | $H_2$:ester molar ratio | LHSV $hr^{-1}$ | Ester Conversion (mol %) | Selectivity (mol %) | | | |
|---|---|---|---|---|---|---|---|---|
| | | | | | THF | BuOH | BL | BD |
| 7 | 180 | 269:1 | 0.35 | 30.9 | 2.1 | 0.4 | 43.4 | 53.9 |
| 8 | 220 | 266:1 | 0.36 | 65.7 | 4.9 | 0.7 | 47.0 | 47.2 |

Notes:
See the notes to Table I for the meaning of the abbreviations

EXAMPLES 9 to 24

Using the apparatus of the drawing and a catalyst volume of 50 ml in each case, some further experiments were carried out under the conditions, and with the results, listed in Table IV. Prior to use the copper chromite catalyst was carefully reduced by extended treatment with an $H_2$ in $N_2$ mixture over a period of days at a temperature below 200° C. The ester used was diethyl maleate. The compositions of the catalysts A to D are listed in Table I. The abbreviations in Table IV are the same as for Tables II and III. The abbreviation "GHSV" means gaseous hourly space velocity, which is measured in $hr^{-1}$ after conversion to 0° C. and 1 bar. The figures under the heading "Ester conversion" are in mol %. As with Tables II and III the selectivities to minor byproducts, such as 2-ethoxytetrahydrofuran and 2-ethoxybutane-1,4-diol are not listed.

TABLE IV

| Example No. | Catalyst | Temperature °C. | Pressure bar | LHSV $hr^{-1}$ | GHSV $hr^{-1}$ | $H_2$:ester molar ratio | Ester Conversion | Selectivity mol % | | | |
|---|---|---|---|---|---|---|---|---|---|---|---|
| | | | | | | | | THF | BuOH | BL | BD |
| 9 | A | 172 | 29.0 | 0.34 | 11847 | 252:1 | 72.1 | 5.9 | 0.1 | 39.7 | 63.4 |
| 10 | A | 171 | 28.9 | 0.19 | 11826 | 456:1 | 94.7 | 5.1 | 0.1 | 31.0 | 63.4 |
| 11 | A | 177 | 28.6 | 0.34 | 13767 | 291:1 | 87.5 | 7.0 | 0.2 | 32.3 | 60.0 |
| 12 | A | 177 | 42.4 | 0.34 | 13767 | 294:1 | 95.6 | 6.6 | 0.2 | 17.1 | 74.9 |
| 13 | A | 177 | 56.3 | 0.34 | 13767 | 295:1 | 97.3 | 6.2 | 0.2 | 9.1 | 84.1 |
| 14 | A | 231 | 28.3 | 0.20 | 8360 | 313:1 | 98.3 | 52.2 | 11.6 | 26.1 | 10.1 |
| 15 | B | 170 | 28.6 | 0.34 | 11847 | 253:1 | 53.8 | 6.3 | 0.1 | 40.0 | 53.6 |
| 16 | B | 189 | 28.9 | 0.34 | 11847 | 253:1 | 86.6 | 11.6 | 0.3 | 39.7 | 48.3 |
| 17 | B | 209 | 28.9 | 0.34 | 11847 | 253:1 | 99.3 | 25.3 | 1.7 | 40.5 | 32.2 |
| 18 | B | 183 | 41.4 | 0.34 | 11847 | 253:1 | 89.0 | 9.3 | 0.2 | 22.7 | 67.8 |
| 19 | B | 171 | 29.2 | 0.35 | 24049 | 494:1 | 67.3 | 5.6 | 0.1 | 36.1 | 58.0 |
| 20 | C | 170 | 28.7 | 0.34 | 11846 | 254:1 | 45.5 | 6.5 | 0.2 | 41.1 | 52.1 |
| 21 | C | 189 | 28.8 | 0.34 | 11847 | 252:1 | 75.9 | 11.1 | 0.4 | 44.3 | 44.0 |
| 22 | C | 209 | 29.0 | 0.34 | 11847 | 253:1 | 95.0 | 21.1 | 1.2 | 45.8 | 31.6 |
| 23 | D | 170 | 28.6 | 0.34 | 11780 | 253:1 | 84.6 | 11.0 | 0.2 | 33.3 | 52.0 |
| 24 | D | 189 | 43.0 | 0.34 | 13370 | 286:1 | 99.7 | 13.1 | 1.4 | 18.0 | 63.9 |

EXAMPLES 25 to 29

Table V lists results for hydrogenolysis of diethyl maleate using two reactors of the type illustrated in the drawing connected in series. In Examples 25, and 27 to 29, all of the diethyl maleate is supplied to the first reactor; in Example 26 50% of the ester is supplied to the first reactor and 50% as a "cold shot" to the second reactor. The abbreviations are the same as for Tables II to IV. Again, the selectivities to minor byproducts have not been listed.

TABLE V

| Example No. | 25 | 26 | 27 | 28 | 29 |
|---|---|---|---|---|---|
| First reactor | | | | | |
| LHSV (hr$^{-1}$) | 0.34 | 0.35 | 0.67 | 0.34 | 0.67 |
| H$_2$:ester molar ratio | 250:1 | 490:1 | 301:1 | 290:1 | 301:1 |
| Temperature (°C.) | 194 | 171 | 190 | 190 | 190 |
| Pressure (bar) | 28.8 | 29.1 | 41.4 | 41.7 | 41.4 |
| Succinate conversion (%) | 89.7 | 63.9 | 79.4 | 93.3 | 79.4 |
| Second reactor | | | | | |
| Feed Composition (mol %) | | | | | |
| DEM | 0.00 | 31.64 | 0.00 | 0.00 | 0.00 |
| DES | 3.70 | 12.36 | 8.33 | 2.52 | 8.33 |
| BL | 12.28 | 5.90 | 8.49 | 7.92 | 8.49 |
| BD | 14.96 | 10.77 | 18.80 | 21.71 | 18.80 |
| THF | 4.09 | 0.91 | 2.65 | 3.19 | 2.65 |
| BuOH | 0.16 | 0.03 | 0.08 | 0.12 | 0.08 |
| EtOH | 64.81 | 38.39 | 61.64 | 64.54 | 61.64 |
| Overall LHSV (hr$^{-1}$) | | | | | |
| Overall H$_2$:ester | | | | | |
| molar ratio | 250:1 | 252:1 | 301:1 | 300:1 | 301:1 |
| Temperature (°C.) | 168 | 170 | 170 | 171 | 170 |
| Overall conversion (%) | 97.2 | 55.1 | 90.8 | 99.6 | 94.8 |
| Overall selectivity (%) | | | | | |
| THF | 14.8 | 6.0 | 9.8 | 17.1 | 10.9 |
| BuOH | 0.6 | 0.2 | 0.3 | 0.6 | 0.3 |
| BL | 20.9 | 36.7 | 14.1 | 12.1 | 12.3 |
| BD | 63.7 | 57.2 | 75.9 | 70.3 | 76.5 |

EXAMPLE 30

The general procedure of Example 1 is repeated using, in place of diethyl maleate, each of the following materials: dimethyl succinate; diethyl succinate; diethyl fumarate; a mixture of diethyl maleate and diethyl fumarate; dimethyl maleate; a mixture of dimethyl maleate and dimethyl fumarate; di-n-propyl maleate; and di-i-propyl maleate. Similarly good results are obtained in each case.

What is claimed is:

1. A continuous process for the production of butane-1,4-diol which comprises:
   providing a plurality of hydrogenolysis zones, including a first hydrogenolysis zone and at least one other hydrogenolysis zone connected in series therewith, each of which contains a charge of a reduced copper chromite catalyst which contains, before reduction, from about 25 to about 45% by weight of copper and from about 20 to about 34% by weight of chromium;
   supplying to the first hydrogenolysis zone at a first feed temperature in the range of from about 170° C. to about 190° C. a vaporous feed stream containing hydrogen and a di-(C$_1$ to C$_3$ alkyl) ester of a C$_4$ dicarboxylic acid at an H$_2$:ester molar ratio of from about 150:1 to about 800:1 and at a rate corresponding to a liquid hourly space velocity of the ester of from about 0.1 to about 0.6 hr$^{-1}$;
   supplying to the other, or to each other, hydrogenolysis zone at a further feed temperature of from about 160° C. to about 175° C. a vaporous stream comprising reaction products from the immediately preceding hydrogenolysis zone, said further feed temperature being, in respect of the other, or in respect of at least one other, hydrogenolysis zone lower than said first feed temperature;
   maintaining the plurality of hydrogenolysis zones at a pressure in the range of from about 25 bar to about 75 bar; and
   recovering a product mixture containing butane-1,4-diol.

2. A process according to claim 1, in which the pressure is in the range of from about 35 bar to about 45 bar.

3. A process according to claim 1, in which the ester is selected from diethyl maleate, diethyl fumarate and mixtures thereof.

4. A process according to claim 1, in which the catalyst has an internal surface area of at least about 30 sq. m. per gram.

5. A process according to claim 1, in which the catalyst has an internal surface area of at least about 60 sq. m. per gram.

6. A process according to claim 1, in which a vaporous mixture containing ester and hydrogen is passed over the catalyst at a gaseous hourly space velocity of from about 2500 to about 85,000 hr$^{-1}$.

7. A process according to claim 1, in which the first hydrogenolysis zone is operated under adiabatic conditions.

8. A process according to claim 7, in which the or each other hydrogenolysis zone is operated under adiabatic conditions.

9. A process according to claim 1, in which the catalyst is a reduced stabilized copper chromite catalyst containing not more than about 15% by weight of at least one stabilizer selected from barium and manganese.

10. A process according to claim 9, in which the catalyst contains, before reduction, from about 32 to about 38% by weight of copper and from about 22 to about 30% by weight of chromium.

11. A process according to claim 1, in which the catalyst contains, before reduction, from about 32 to about 38% by weight of copper and from about 22 to about 30% by weight of chromium.

* * * * *

UNITED STATES PATENT AND TRADEMARK OFFICE
CERTIFICATE OF CORRECTION

PATENT NO. : 4,584,419
DATED : April 22, 1986
INVENTOR(S) : Mohammad Sharif et al.

It is certified that error appears in the above-identified patent and that said Letters Patent is hereby corrected as shown below:

The name of the Assignee should read "Davy McKee (London) Limited and not "Davy McKee Ltd.";

In Table IV, Example No. 9, under the heading "BD" please delete "63.4" and substitute therefor -- 52.7 --;

In Table V at Column 11, line 17, under the heading "25" please add -- 0.17 --; under the heading "26" please add -- 0.34 --; under the heading "27" please add -- 0.34 --; under the heading "28" please add -- 0.25 --; and under the heading "29" please add -- 0.34 --;

In Claim 1, Column 11, line 45 please delete "34%" and substitute therefor -- 35% --.

Signed and Sealed this

Ninth Day of December, 1986

Attest:

DONALD J. QUIGG

Attesting Officer

Commissioner of Patents and Trademarks